United States Patent
Falkowski et al.

(10) Patent No.: US 10,696,558 B2
(45) Date of Patent: Jun. 30, 2020

(54) ZEOLITIC IMIDAZOLATE FRAMEWORK MATERIALS, THEIR SYNTHESIS AND USE

(71) Applicant: ExxonMobil Research and Engineering Company, Annandale, NJ (US)

(72) Inventors: Joseph M. Falkowski, Hampton, NJ (US); David C. Calabro, Bridgewater, NJ (US); Yi Du, Coopersburg, PA (US); Mobae Afeworki, Phillipsburg, NJ (US); Simon C. Weston, Annandale, NJ (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 194 days.

(21) Appl. No.: 15/924,597

(22) Filed: Mar. 19, 2018

(65) Prior Publication Data
US 2018/0273390 A1    Sep. 27, 2018

Related U.S. Application Data

(60) Provisional application No. 62/474,125, filed on Mar. 21, 2017.

(51) Int. Cl.

| | | |
|---|---|---|
| *C01B 39/04* | (2006.01) | |
| *C07F 3/06* | (2006.01) | |
| *C07F 15/06* | (2006.01) | |
| *B01J 31/16* | (2006.01) | |
| *C07D 235/04* | (2006.01) | |
| *C07D 471/04* | (2006.01) | |
| *C07F 19/00* | (2006.01) | |
| *C01B 39/02* | (2006.01) | |
| *B01D 71/02* | (2006.01) | |
| *B01D 69/14* | (2006.01) | |
| *B01J 20/22* | (2006.01) | |
| *C07C 7/13* | (2006.01) | |
| *C07C 53/10* | (2006.01) | |

(52) U.S. Cl.
CPC ............ *C01B 39/04* (2013.01); *B01D 69/141* (2013.01); *B01D 71/028* (2013.01); *B01J 20/226* (2013.01); *B01J 31/1691* (2013.01); *C01B 39/026* (2013.01); *C07C 7/13* (2013.01); *C07D 235/04* (2013.01); *C07D 471/04* (2013.01); *C07F 3/06* (2013.01); *C07F 15/06* (2013.01); *C07F 19/005* (2013.01); *C01P 2002/72* (2013.01); *C01P 2004/03* (2013.01); *C07C 53/10* (2013.01)

(58) Field of Classification Search
CPC .................................. C07F 3/06; C07F 15/06
See application file for complete search history.

(56) References Cited

U.S. PATENT DOCUMENTS

| | | |
|---|---|---|
| 8,480,792 B2 | 7/2013 | Yaghi et al. |
| 8,636,969 B2 | 1/2014 | Weston et al. |
| 8,907,102 B2 | 12/2014 | Weston et al. |
| 2013/0197235 A1 | 8/2013 | Thompson et al. |

OTHER PUBLICATIONS

Banerjee et al., "Control of pore size and functionality in isoreticular zeolitic imidazolate frameworks and their carbon dioxide selective capture properties", J. Am. Chem. Soc., 2009, vol. 131, pp. 3875-3877.
Banerjee et al., "High-throughput synthesis of zeolitic imidazolate frameworks and applicaton to CO2 capture", Science, 2008, vol. 319, pp. 939-942.
Du et al., "New high- and low-temperature phase changes of ZIF-7: elucidation and prediction of the thermodynamics of transitions", J. Am. Chem. Soc., vol. 137, pp. 13603-13611.
Eum et al., "Highly tunable molecular sieving and adsorption properties of mixed-linker zeolitic imidazolate frameworks", J. Am. Chem. Soc., 2015, vol. 137, pp. 4191-4197.
Hayashi et al., "Zeolite A imidazolate frameworks", Nature Materials, 2007, vol. 6, pp. 501-506.
Mason et al., "Methane storage in flexible metal-organic frameworks with intrinsic thermal management", Nature, 2015, vol. 527, 357-361.
Morris et al . . . , "A combined experimental-computational investigation of carbon dioxide capture in a series of isoreticular zeolitic imidazolate frameworks", J. Am. Chem. Soc., 2010, vol. 132, pp. 11006-11008.
Park et al., "Exceptional chemical and thermal stability of zeolitic imidazolate frameworks", PNAS, 2006, vol. 103, pp. 10186-10191.
Phan et al., "Synthesis, structure, and carbon dioxide capture properties of zeolitic imidazolate frameworks", Am Chem. Res., 2009, vol. 43, pp. 58-67.
Rashidi et al., "Synthesis, characterization, and tunable adsorption and diffusion properties of hybrid ZIF-7-90 frameworks", AIChE J., 2016, vol. 62, pp. 525-537.
Thompson et al., "Hybrid zeolitic imidazolate frameworks: controlling framework porosity and functionality by mixed-linker synthesis", Chem. Materials, 2012, vol. 24, pp. 1930-1936.
Thompson et al., "Tunable CO2 adsorbents by mixed-linker synthesis and postsynthetic modification of zeolitic imidazolate frameworks", J. Phys. Chem. C, 2013, vol. 117, pp. 8198-8207.

(Continued)

*Primary Examiner* — Joseph R Kosack
(74) *Attorney, Agent, or Firm* — Priya G. Prasad

(57) ABSTRACT

A novel zeolitic imidazolate framework material comprises a partially saturated benzimidazole or a partially saturated substituted benzimidazole as a linking ligand, optionally together with unsaturated benzimidazole or an unsaturated substituted benzimidazole as a further linking ligand.

18 Claims, 8 Drawing Sheets

(56) References Cited

OTHER PUBLICATIONS

Wang et al., "Colossal cages in zeolitic imidazolate frameworks as selective carbon dioxide reservoirs", Nature, 2008, vol. 453, pp. 207-212.
Borjigin et al., "A microporous metal-organic framework with high stability for GC separation of alcohols from water", Chem. Commun., 2012, 48, 7613-7165.
The International Search Report and Written Opinion of PCT/US2018/023246 dated Jul. 4, 2018.

ZEOLITIC IMIDAZOLATE FRAMEWORK MATERIALS, THEIR SYNTHESIS AND USE

CROSS-REFERENCE TO RELATED APPLICATIONS

This application claims the benefit of U.S. Provisional Application No. 62/474,125, filed on Mar. 21, 2017, the entire contents of which are incorporated herein by reference.

FIELD

The present disclosure relates to novel zeolitic imidazolate framework materials (ZIFs) and to the synthesis of these materials and their use, particularly in sorptive applications.

BACKGROUND

One known family of porous crystalline materials are zeolitic materials, which are based on the 3-dimensional, four-connected framework structure defined by corner-sharing [$TO_4$] tetrahedra, where T is any tetrahedrally coordinated cation. Among the known materials in this family are silicates that contain a three-dimensional microporous crystal framework structure of [$SiO_4$] corner sharing tetrahedral units, aluminosilicates that contain a three-dimensional microporous crystal framework structure of [$SiO_4$] and [$AlO_4$] corner sharing tetrahedral units, aluminophosphates that contain a three-dimensional microporous crystal framework structure of [$AlO_4$] and [$PO_4$] corner sharing tetrahedral units, and silicoaluminophosphates (SAPOs), in which the framework structure is composed of [$SiO_4$], [$AlO_4$] and [$PO_4$] corner sharing tetrahedral units. Included in the zeolitic family of materials are over 200 different porous framework types, many of which have great commercial value as catalysts and adsorbents.

Zeolitic imidazolate frameworks or ZIFs have properties similar to inorganic zeolitic materials. ZIFs are based on a [$M(IM)_4$] tetrahedral coordination bonding environment in which IM is an imidazolate-type linking moiety and M is a transition metal. These materials are generally referred to as zeolitic imidazolate frameworks or ZIFs since the angle formed by imidazolates (IMs) when bridging transition metals is similar to the ~145° angle of the Si—O—Si bond in zeolites. ZIF counterparts of a large number of known zeolite structures have been produced. In addition, porous framework types, hitherto unknown to zeolites, have also been produced. Discussion of this research can be found in, for example, the following publications from Yaghi and his co-workers: "Exceptional Chemical and Thermal Stability of Zeolitic Imidazolate Frameworks", Proceedings of the National Academy of Sciences of U.S.A., Vol. 103, 2006, pp. 10186-91, "Zeolite A Imidazolate Frameworks", Nature Materials, Vol. 6, 2007, pp. 501-6, "High-Throughput Synthesis of Zeolitic Imidazolate Frameworks and Application to $CO_2$ Capture", Science, Vol. 319, 2008, pp. 939-43, "Colossal Cages in Zeolitic Imidazolate Frameworks as Selective Carbon Dioxide Reservoirs", Nature, Vol. 453, 2008, pp. 207-12, "Control of Pore Size and Functionality in Isoreticular Zeolitic Imidazolate Frameworks and their Carbon Dioxide Selective Capture Properties". Journal of the American Chemical Society. Vol. 131, 2009, pp. 3875-7, "A Combined Experimental-Computational Investigation of Carbon Dioxide Capture in a Series of Isoreticular Zeolitic Imidazolate Frameworks", Journal of the American Chemical Society, Vol. 132, 2010, pp. 11006-8, and "Synthesis, Structure, and Carbon Dioxide Capture Properties of Zeolitic Imidazolate Frameworks", Accounts of Chemical Research, Vol. 43, 2010, pp. 58-67.

Several ZIFs are known to have good thermal and chemical stability, high microporosity, and high internal surface area. ZIFs have therefore created substantial interest for potential use in diffusive and adsorptive separations. In particular, ZIF-7 (in which the imidazolate-type linking moiety is benzimidazole) has been the focus of extensive research efforts, at least partly because the material undergoes an unusual and reversible phase change transition from a narrow-pore to large-pore form both on heating and during adsorption of guest molecules. See, for example, Du, Y.; Wooler, B.; Nines, M.; Kortunov, P.; Paur, C. S.; Zengel, J.; Weston, S. C.; Ravikovitch, P. L *J. Am. Chem. Soc.* 2015, 137, 13603-13611. This represents a significant opportunity for the potential use of ZIF-7 and related structures in gas separation and storage.

Of all the ZIFs discovered, only a few are known to undergo such displacive transitions from a nearly nonporous to a porous structure upon adsorption of guest molecules. This guest responsive phase change usually results in a step change in the adsorption isotherm. Other examples of ZIF materials exhibiting this property are ZIF-9 and EMM-19. In these materials, the nature of the adsorption is fixed; the pressure in which phase change and subsequent adsorption occurs is an intrinsic property of the material and the guest being adsorbed and is not tunable. The ability to tune these adsorption properties synthetically has been a goal of many researchers. Some $CO_2$ sorbent materials do exhibit this synthetic tunability (see, for example, Mason, J. A.; Oktawiec, J.; Taylor, M. K.; Hudson, M. R.; Rodriguez, J.; Bachman, J. E.; Gonzalez, M. I.; Cervellino, A.; Guagliardi, A.; Brown, C. M.; Llewellyn, P. L.; Masciocchi, N.; Long, J. R. *Nature* 2015, 527, 357-361). However, it is reliant on the adsorption of a reactive gas such as $CO_2$ and is not a general technique. Other researchers have attempted to use a "mixed-linker approach" to tune the adsorption properties of ZIF-7 (see, for example, Thompson, J. A.; Blad, C. R.; Brunelli, N. A.; Lydon, M. E.; Lively, R. P.; Jones, C. W.; Nair, S. *Chem. Mater.* 2012, 24, 1930-1936). In the cited work, linkers such as 2-methylimidazole or 2-carboxylimidazole were incorporated into ZIF-7 in an attempt to modulate the adsorption properties of the ZIF-7. However, this approach proves to be difficult because the doping of ZIF-7 with any other imidazole linker is difficult synthetically often resulting in materials with only a small amount of the desired dopant linker actually incorporating into the material.

There is therefore a need for new methods of tuning the composition and adsorption properties of zeolitic imidazolate frameworks, especially those, such as ZIF-7, which exhibit phase change transitions.

SUMMARY

According to the invention, it has now been found that a mixed linker approach, in which part or all of the benzimidazole linking ligand is replaced by a partially saturated benzimidazole, such as 4,5,6,7-tetrahydrobenzimidazole, or a partially saturated substituted benzimidazole, such as 4,5,6,7-tetrahydro-3H-imidazo[4,5-c]pyridine, allows ligand incorporation into ZIF framework structures, such as ZIF-7, at ratios similar to their starting reaction mixtures. This allows for the precise control of the phase change behavior present in these materials and as a result directly influences the adsorption properties of the resulting material.

Thus, in one aspect, the invention resides in a zeolitic imidazolate framework material comprising a partially saturated benzimidazole or a partially saturated substituted benzimidazole as a linking ligand.

In a further aspect, the invention resides in a zeolitic imidazolate framework material comprising zinc and 4,5,6,7-tetrahydrobenzimidazole.

In yet a further aspect, the invention resides in a zeolitic imidazolate framework material comprising zinc and 4,5,6,7-tetrahydro-3H-imidazo[4,5-c]pyridine.

In another aspect, the invention resides in a method of making a zeolitic imidazolate framework material comprising the step of reacting a mixture of a source of a partially saturated benzimidazole or a source of a partially saturated substituted benzimidazole with a source of zinc in the presence of a solvent at a temperature sufficient to form the zeolitic imidazolate framework material. The temperature may preferably be at least 20° C.

In still another aspect, the invention resides in a method of adsorbing an element or compound, such as methane, from a fluid, the method comprising the step of contacting the fluid with a zeolitic imidazolate framework material as described herein.

DETAILED DESCRIPTION OF THE EMBODIMENTS

Figure 1:
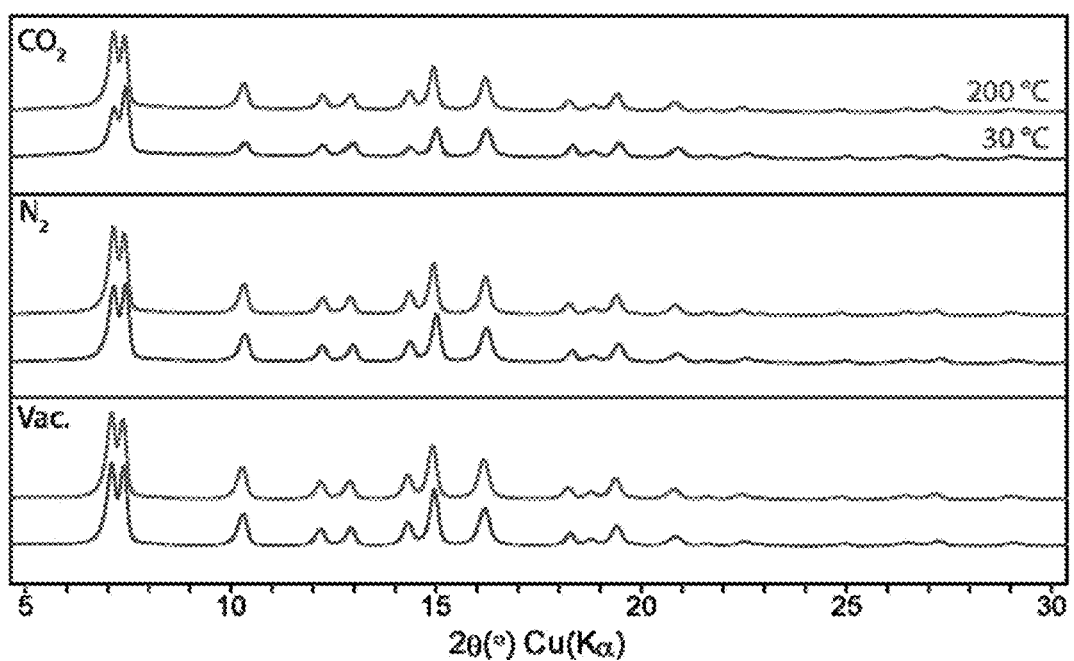
FIG. 1 compares the X-ray diffraction patterns of the EMM-36-100 material of Example 1 measured at 200° C. and 30° C. and conducted in vacuum (<$10^{-3}$ mbar), nitrogen (1 bar), and carbon dioxide (1 bar).

Disclosed herein are certain novel zeolitic imidazolate framework (ZIF) compositions comprising a partially saturated benzimidazole or a partially saturated substituted benzimidazole as a linking ligand, optionally in combination with unsaturated benzimidazole or an unsaturated substituted benzimidazole as a further linking ligand. Also disclosed are methods of producing these novel ZIF materials with different controlled levels of partially saturated benzimidazole or partially saturated substituted benzimidazole in the structure and methods of using the resultant ZIF materials in adsorption of gases, such as methane.

As used herein, the terms "unsaturated benzimidazole", "benzimidazole" or simply "BIM" are used interchangeably to mean the heterocyclic aromatic compound, $C_7H_6N_2$, (see formula I) which has unsaturation and a single hydrogen atom at each of the 4, 5, 6 and 7 positions of the benzene ring.

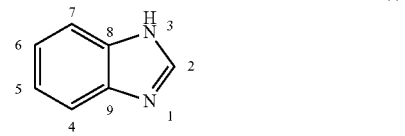

(I)

As used herein, the term "partially saturated benzimidazole" means a heterocyclic compound comprising benzimidazole, in which the unsaturation at some or all of the 4, 5, 6 and 7 positions on the benzene ring is replaced with additional hydrogen atoms. One example of a partially saturated benzimidazole comprises 4,5,6,7-tetrahydrobenzimidazole or, in some cases, abbreviated herein to 4H-BIM (see formula II).

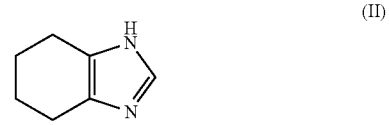

(II)

As used herein, the term "unsaturated substituted benzimidazole" means a heterocyclic compound comprising benzimidazole which has unsaturation and at each of the 4, 5, 6 and 7 positions on the benzene ring and one or more of the carbon atoms at the 4, 5, 6, and 7 positions has been replaced with a heteroatom including, but not limited to, nitrogen, oxygen or sulfur. One example of an unsaturated substituted benzimidazole comprises 5-azabenzimidazole (see formula III).

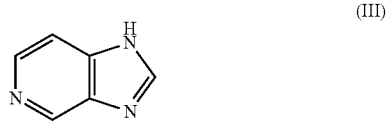

(III)

As used herein, the term "partially saturated substituted benzimidazole" means a heterocyclic compound comprising benzimidazole, in which the unsaturation at some or all of the 4, 5, 6 and 7 positions on the benzene ring is replaced with additional hydrogen atoms and one or more of the carbon atoms at the 4, 5, 6, and 7 positions has been replaced with a heteroatom including, but not limited to, nitrogen, oxygen or sulfur. One example of a partially saturated substituted benzimidazole comprises 4,5,6,7-tetrahydro-3H-imidazo[4,5-c]pyridine, abbreviated herein to 4H-IMP (see formula IV).

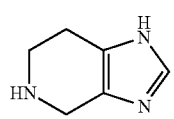

(IV)

In some embodiments, where the linking ligand comprises 4,5,6,7-tetrahydrobenzimidazole (4H-BIM) or 4,5,6,7-tetrahydro-3H-imidazo[4,5-c]pyridine, optionally in a mixed ligand system also comprising benzimidazole or 5-azabenzimidazole, the ZIF synthesis is conducted in the presence of a solvent. In this case, a novel ZIF material is produced which is designated herein as EMM-36, or more specifically as EMM-36-##, where ## refers to the mol % of 4H-BIM or 4H-IMP of the total organic linkers in the final material. EMM-36-## has the SOD framework type and is closely structurally related to ZIF-7. EMM-36-100 (where 4H-BIM or 4H-IMP is the only organic linker in the structure) is isostructural with the large pore phase of ZIF-7 and is found to exhibit the unique property—for a porous material—of having essentially no nitrogen adsorption at 77 K while adsorbing $CO_2$ at room temperature. Surprisingly and unlike the nearly isostructural ZIF-7 (formed from benzimidazole as the only organic linker), EMM-36-100 does not exhibit phase change behavior at room temperature. This property and the adsorption behavior of other EMM-36-## materials are examined further in the Examples.

EMM-36 has an X-ray diffraction pattern similar to that of ZIF-7 and includes the characteristic lines listed in Table 1 below:

TABLE 1

| Interplanar d-Spacing (Å) | Two-theta | Relative Intensity (100 × I/Io) |
|---|---|---|
| 12.313 | 7.173 | 88.3 |
| 11.8097 | 7.480 | 100 |
| 8.4946 | 10.406 | 33.1 |
| 7.2150 | 12.257 | 21.3 |
| 6.7984 | 13.012 | 20.3 |
| 6.1556 | 14.377 | 24.9 |
| 5.8850 | 15.042 | 63 |
| 5.4460 | 16.263 | 44.8 |
| 4.8362 | 18.330 | 17 |
| 4.6996 | 18.868 | 9.1 |
| 4.5617 | 19.443 | 23.3 |
| 4.2544 | 20.863 | 10.8 |
| 4.0936 | 21.692 | 2.3 |
| 3.9243 | 22.640 | 6.0 |

In other embodiments, where the linking ligand comprises 4,5,6,7-tetrahydrobenzimidazole (4H-BIM) or 4,5,6,7-tetrahydro-3H-imidazo[4,5-c]pyridine (4H-IMP), optionally in a mixed ligand system also comprising benzimidazole or 5-azabenzimidazole, the ZIF synthesis is conducted in the presence of toluene as a structure directing agent. In this case, a further novel ZIF material is produced which is designated herein as EMM-38-##, where ## refers to the mol % of 4H-BIM or 4H-IMP of the total organic linkers in the final material. EMM-38-## has the RHO framework type and is closely structurally related to ZIF-11.

EMM-38 has an X-ray diffraction pattern similar to that of ZIF-11 and includes the characteristic lines listed in Table 2 below:

TABLE 2

| Interplanar d-Spacing (Å) | Two-theta | Relative Intensity (100 × I/Io) |
|---|---|---|
| 20.7068 | 4.264 | 100 |
| 14.5293 | 6.078 | 11.3 |
| 11.9230 | 7.408 | 18.3 |
| 10.3385 | 8.546 | 1.3 |
| 9.1399 | 9.669 | 2.7 |
| 8.0393 | 10.997 | 0.9 |
| 7.3000 | 12.114 | 5.3 |
| 6.9025 | 12.815 | 4.4 |
| 6.4519 | 13.714 | 4.5 |
| 5.9164 | 14.962 | 3.7 |
| 5.6570 | 15.652 | 10.4 |
| 5.2891 | 16.748 | 7.9 |
| 5.0890 | 17.412 | 3.6 |
| 4.8038 | 18.455 | 7.6 |

All X-ray diffraction data reported herein were collected with a Panalytical X'Pert Pro diffraction system with an Xcelerator multichannel detector, equipped with a germanium solid state detector, using copper K-alpha radiation. The diffraction data were recorded by step-scanning at 0.02 degrees of two-theta, where theta is the Bragg angle, and using an effective counting time of 2 seconds for each step. The interplanar spacings, d-spacings, were calculated in Angstrom units, and the relative intensities of the lines, $I/I_0$ is the ratio of the peak intensity to that of the intensity of the strongest line, above background. The intensities are uncorrected for Lorentz and polarization effects. The relative intensities are given in terms of the symbols vs=very strong (75-100), s=strong 50-74), m=medium (25-49) and w=weak (0-24).

In addition to the linking ligands described above the novel ZIF materials disclosed herein comprise one or more metal ions. Suitable metal ions may include one or more divalent transition metals. Suitable metal ions may include one or more zinc ions, one or more cobalt ions and a 1:1 mixture of lithium and boron ions. $Zn^{2+}$ ions are preferred. Further it is to be appreciated that, although the linking ligands are described herein as "imidazole" compounds, this is only for simplicity and in the final ZIF materials these compounds will be present as deprotonated, negatively-charged "imidazolate" species.

In one embodiment, the ZIF materials disclosed herein may be prepared by dissolving a source of desired metal ion(s), such as zinc acetate, and sources of the desired linking ligands in an appropriate solvent to form a reaction mixture and then maintaining this reaction mixture under conditions sufficient to form the crystalline ZIF materials as a precipitate.

In another embodiment, it will be appreciated from the preceding discussion that the selection of the solvent may dictate the structure of the ZIF produced. Thus, suitable solvents include alcohols, such as methanol and ethanol, in which case the ZIF produced may be of the SOD framework type. Alternately, where the solvent includes toluene, optionally together with methanol and/or ethanol, the ZIF produced may be of the RHO framework type.

In yet a further embodiment, techniques such as liquid-assisted grinding or mechanochemical techniques could be utilized to synthesize the disclosed ZIF materials.

The novel ZIF materials disclosed herein may have selectivity for adsorbing a variety of elements and compounds from fluids containing the same. Examples of such elements and compounds comprise hydrogen, nitrogen, oxygen, noble gases, carbon monoxide, carbon dioxide, sulfur dioxide, sulfur trioxide, hydrogen sulfide, ammonia, methane, higher carbon number hydrocarbons, alcohols, amines and mixtures thereof. Examples of hydrocarbons include alkanes, such as ethane, propane, butane, pentane, hexane and octane, and alkenes, such as ethene, propene, butene, hexene and octene. Examples of alcohols include methanol, ethanol, propanol and butanol (e.g., isobutanol, n-butanol, tert-butanol, 2-methyl-1-butanol, 3-methyl-2-butanol, etc.). Examples of amines include methylamine, ethylamine, propylamine and butylamines.

The invention will now be more particularly described with reference to the following non-limiting Examples and the accompanying drawings.

Example 1: Synthesis of EMM-36-100

100 mg of 4,5,6,7-tetrahydrobenzimidazole was dissolved in 10 mL of ethanol and 0.1 mL of $NH_4OH$ (conc.) was added to the solution. To this solution, 0.1 g of $Zn(OAc)_2$ was added and the reaction mixture stirred at room temperature (25° C.) for 16 hours. The product was isolated by filtration, washed with ethanol and dried at 90° C. under air.

FIG. 1 shows X-ray diffraction patterns of the resultant EMM-36-100 measured at 200° C. and 30° C. conducted in vacuum (<$10^{-3}$ mbar, bottom), nitrogen (1 bar, middle), and carbon dioxide (1 bar, top). The results are consistent with the large pore phase of the SOD framework structure under all conditions, suggesting there is no phase change over the whole range of conditions tested.

Figure 2:
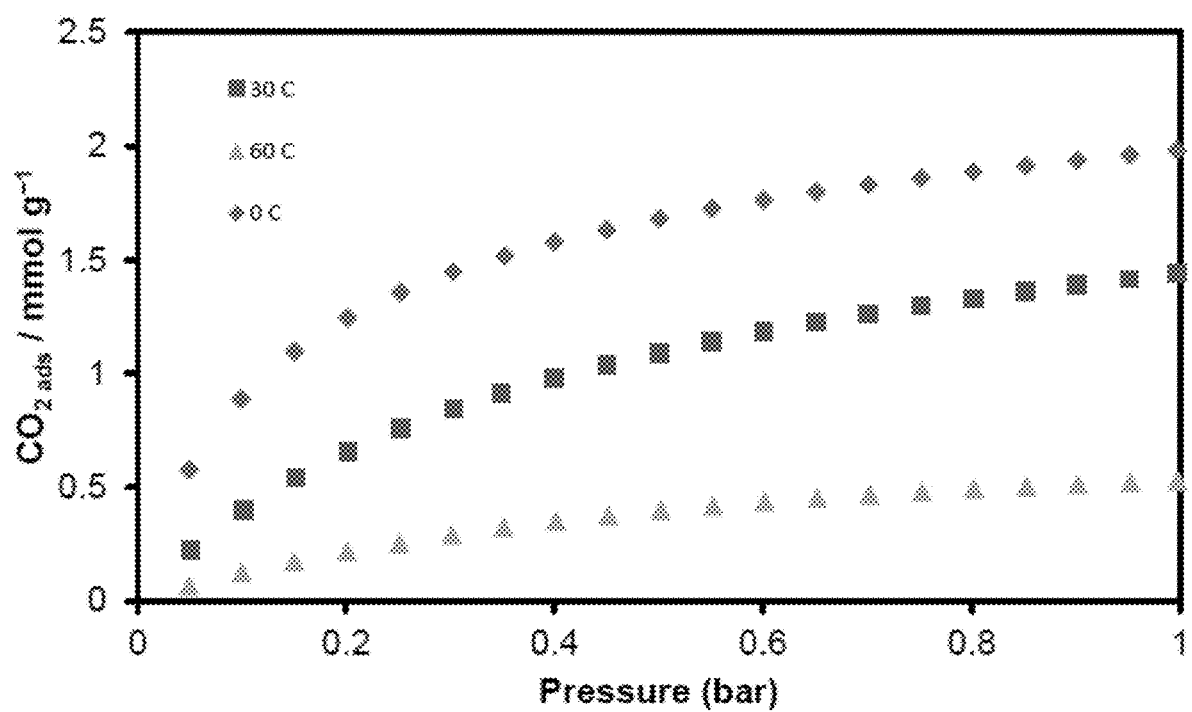
FIG. 2 shows the results of $CO_2$ adsorption isotherms conducted on the EMM-36-100 material of Example 1 at 0° C., 30° C., and 60° C.
Figure 3:
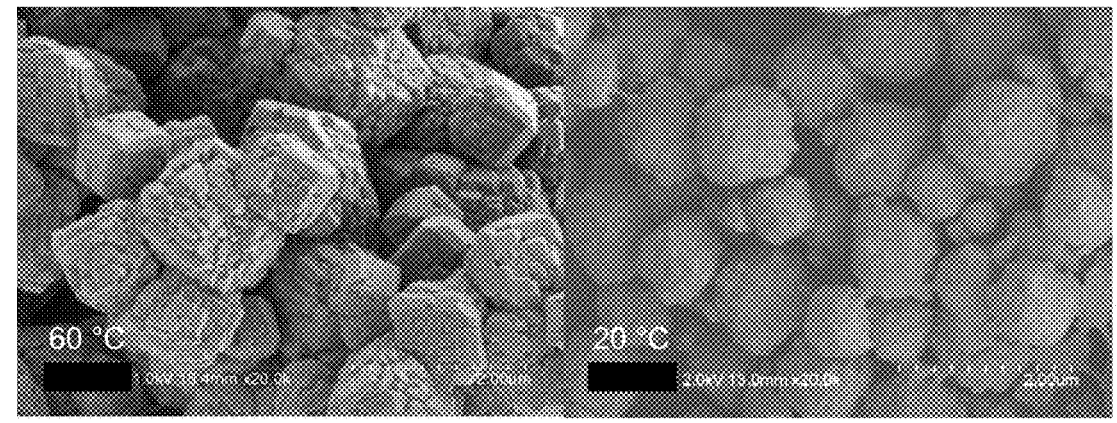
FIG. 3 shows scanning electron micrographs of EMM-36-100 synthesized at 60° C. and 20° C.

FIG. 2 shows the results of $CO_2$ adsorption isotherms conducted on the EMM-36-100 material at 0° C., 30° C., and 60° C. and demonstrates that the material has a Type I isotherm for all temperatures ranging from 20 to 60° C. FIG. 3 shows SEM micrographs of EMM-36-100 synthesized at 20° C. and 60° C. It can be seen that elevating the synthesis temperature results in larger particles with an increase in crystallite size.

Example 2: Synthesis of EMM-36-##

Figure 4:
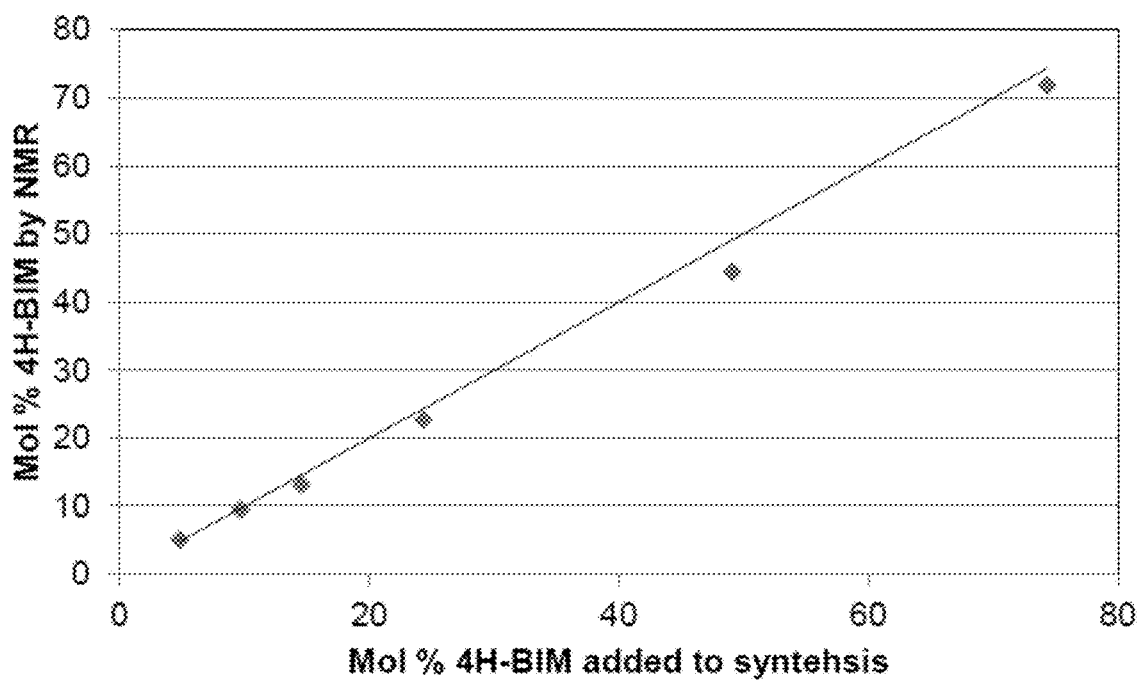
FIG. 4 is a graph of the compositional analysis of EMM-36-## (## representing the mol % of 4H-BIM) performed by liquid-phase NMR against the mol % of 4,5,6,7-tetrahydrobenzimidazole added to the synthesis mixture of Example 2.

The process of Example 1 was repeated but with a series of mixtures of benzimidazole (BIM) with varying quantities from 1 to 99 mol % of 4,5,6,7-tetrahydrobenzimidazole (4H-BIM). Compositional analyses of the resultant EMM-36-## products were performed by liquid-phase $^1H$ NMR and a comparison of those results with the content of the initial synthesis mixtures is shown in FIG. 4. The solid line in FIG. 4 represents the ideal incorporation of the 4,5,6,7-tetrahydrobenzimidazole in the ZIF structure, whereas the diamonds represent the incorporation observed by $^1H$ NMR. It is apparent from FIG. 4 that 4H-BIM and BIM incorporate into the ZIF framework structure at ratios very similar to their starting reaction mixtures. This ability allows for fine control of the composition of EMM-36.

Figure 5:
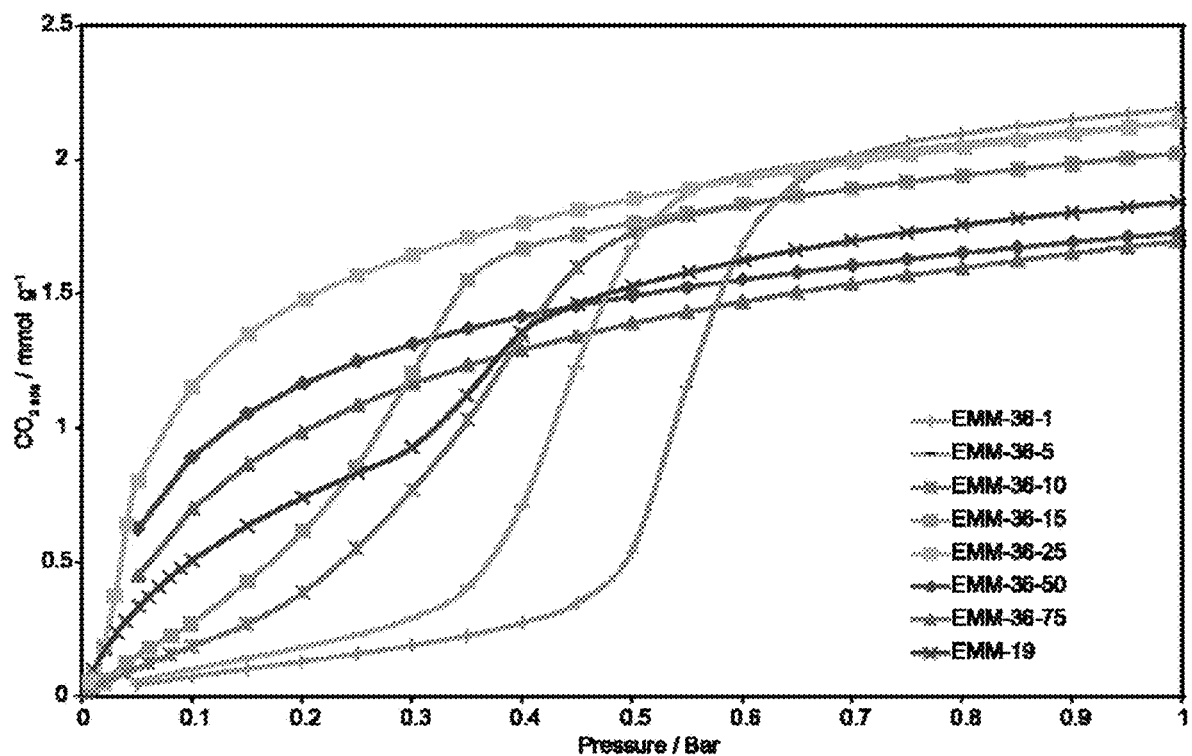
FIG. 5 shows $CO_2$ adsorption isotherms conducted at 30° C. on EMM-19 and various EMM-36-## materials produced according to Example 2.

$CO_2$ adsorption isotherms were conducted at 30° C. on the EMM-36-## products and the results are shown in FIG. 5. It will be seen that EMM-36-## exhibits a stepped isotherm similar to ZIF-7 at low 4H-BIM ratios. As the 4H-BIM content is increased up to 25 mol %, the isotherm step shifts to as low as 0.05 bar. At higher levels of 4H-BIM, a Type I isotherm results.

Figure 6:
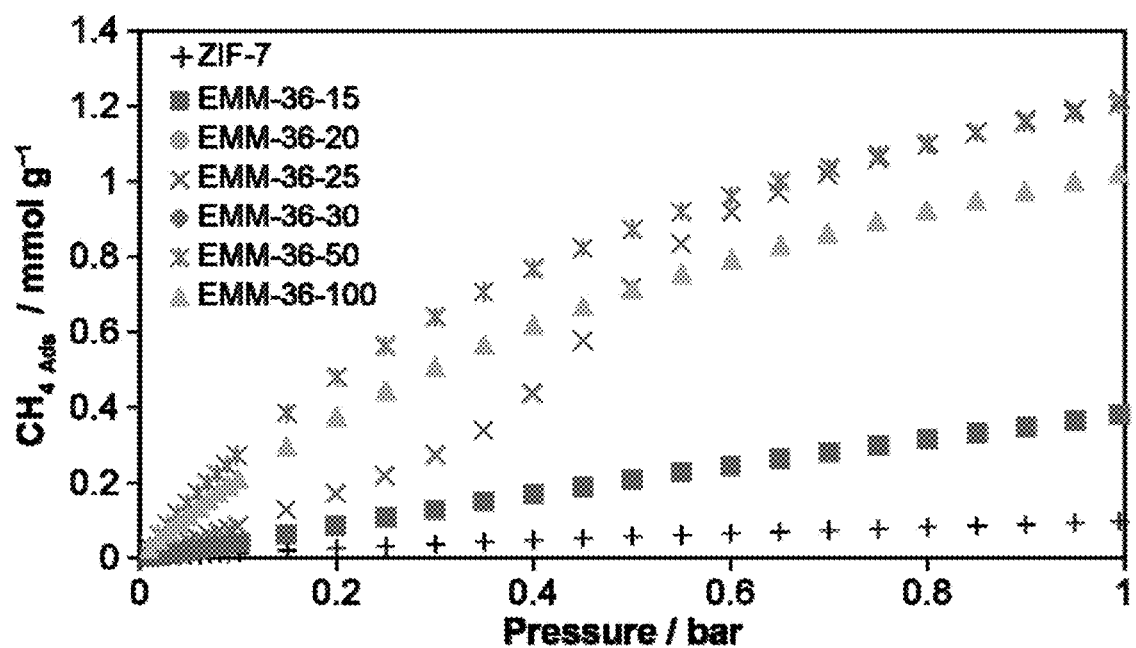
FIG. 6 shows $CH_4$ adsorption isotherms conducted at 30° C. on ZIF-7 and various EMM-36-## materials produced according to Examples 1 and 2.

$CH_4$ adsorption isotherms were also conducted at 30° C. on EMM-36-## materials and the results are shown in FIG. 6. As the 4H-BIM content is increased beyond 15 mol %, the isotherm step occurs below 1 bar. Above about 25 mol % 4H-BIM, the materials remain in the open pore phase throughout the isotherm (above 0.01 bar).

Figure 7:
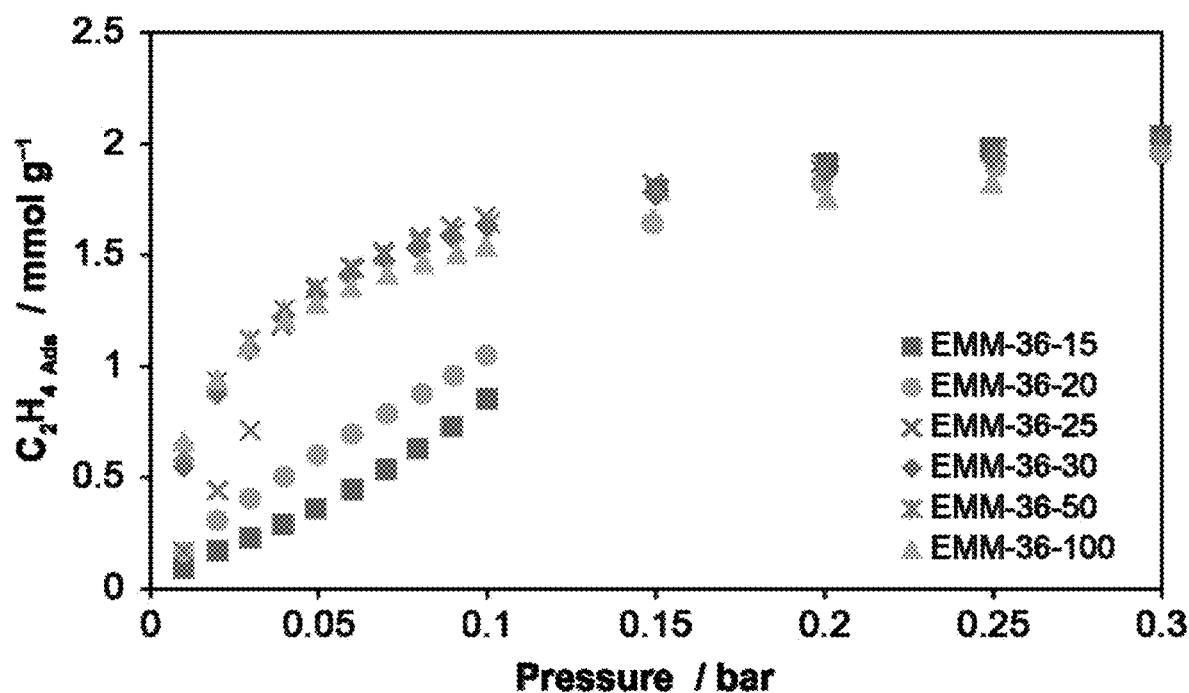
FIG. 7 shows $C_2H_4$ adsorption isotherms conducted at 30° C. on ZIF-7 and various EMM-36-## materials produced according to Examples 1 and 2.

$C_2H_4$ adsorption isotherms were conducted at 30° C. on ZIF-7 as well as the EMM-36-## materials. The results shown in FIG. 7 demonstrate the potential utility of the EMM-36-## materials as $C_2H_4$ adsorbents.

Example 3: Synthesis of EMM-38-##

100 mg of a mixture of 4,5,6,7-tetrahydrobenzimidazole (4H-BIM) with varying amounts benzimidazole (BIM) was dissolved in 10 mL of methanol/toluene (1:1) and 0.1 mL of $NH_4OH$ (conc.) added to the solution. To this solution, 0.1 g of $Zn(OAc)_2$ was added and the reaction mixture stirred at room temperature (25° C.) for 16 hours. The product is filtered out, washed with ethanol and dried at 70° C. under air.

Figure 8:
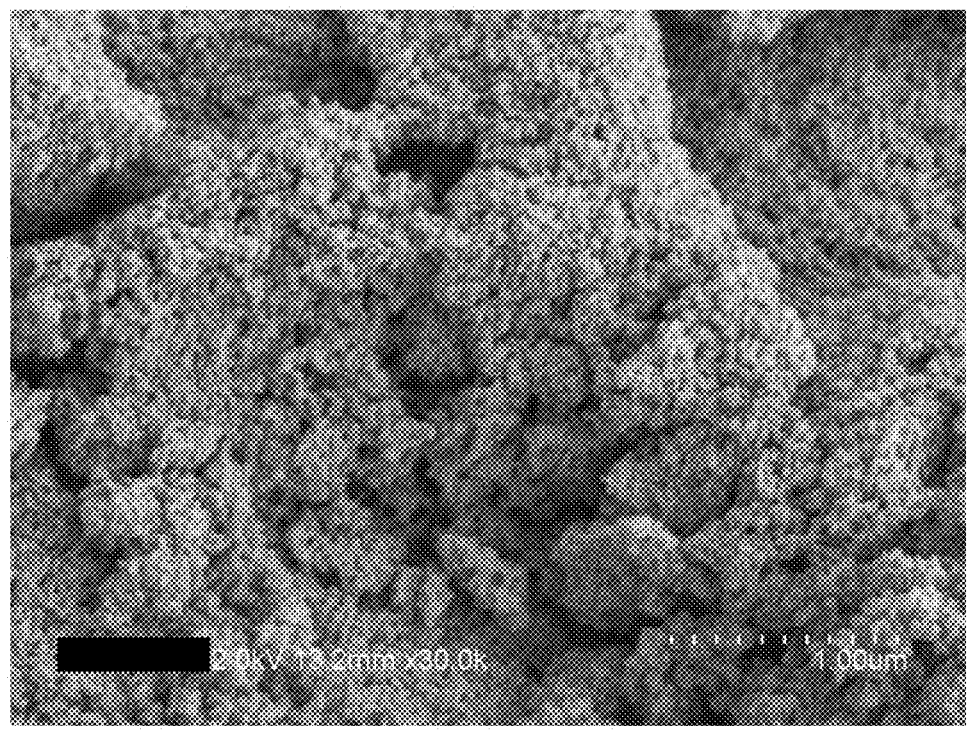
FIG. 8 shows a scanning electron micrograph (SEM) of the EMM-38-100 material of Example 3.
Figure 9:
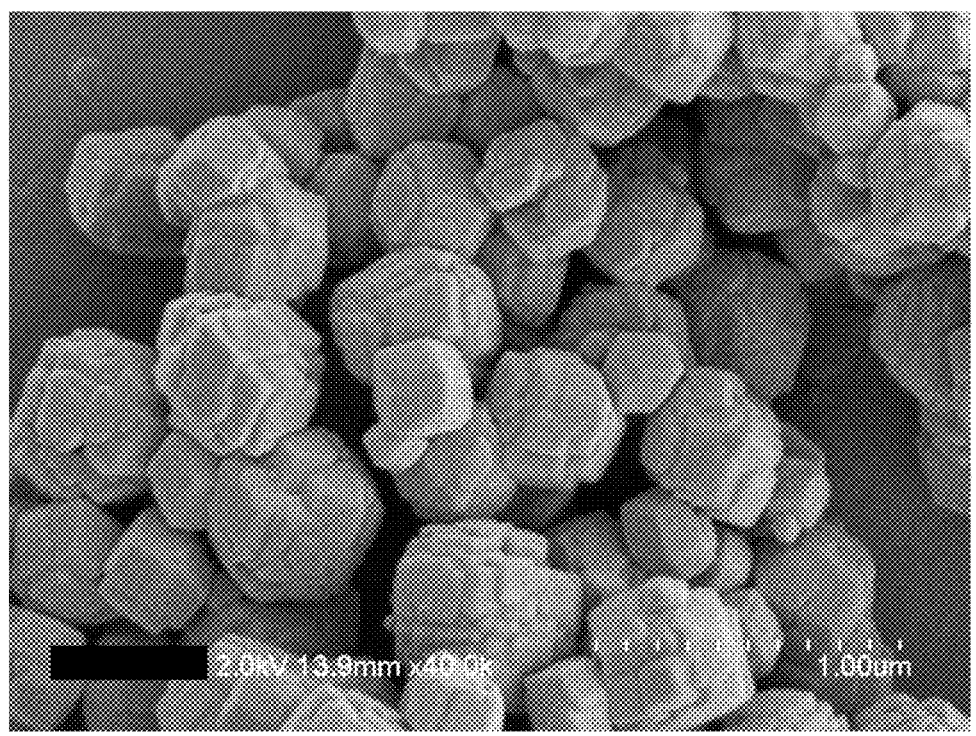
FIG. 9 shows a scanning electron micrograph (SEM) of the EMM-38-25 material of Example 3.
Figure 10:
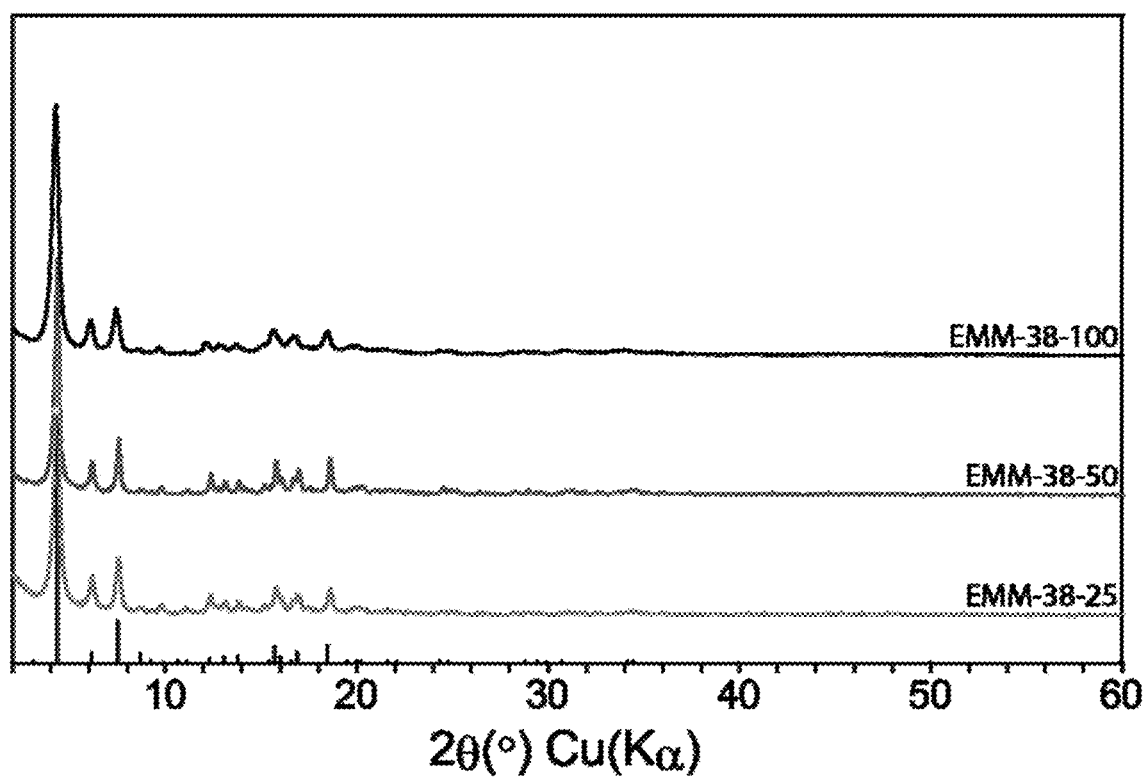
FIG. 10 shows powder X-ray diffraction patterns of EMM-38-## materials of Example 3 with varying loadings of 4,5,6,7-tetrahydrobenzimidazole.

The SEM of the resultant EMM-38-100 product (containing 100 mol % 4H-BIM) is shown in FIG. 8 and the SEM of the EMM-38-25 product (containing 25 mol % 4H-BIM) is shown in FIG. 9. Powder X-ray diffraction patterns of the EMM-38-25, EMM-38-50 and EMM-38-100 materials are shown in FIG. 10 exhibiting the RHO framework structure.

Figure 11:
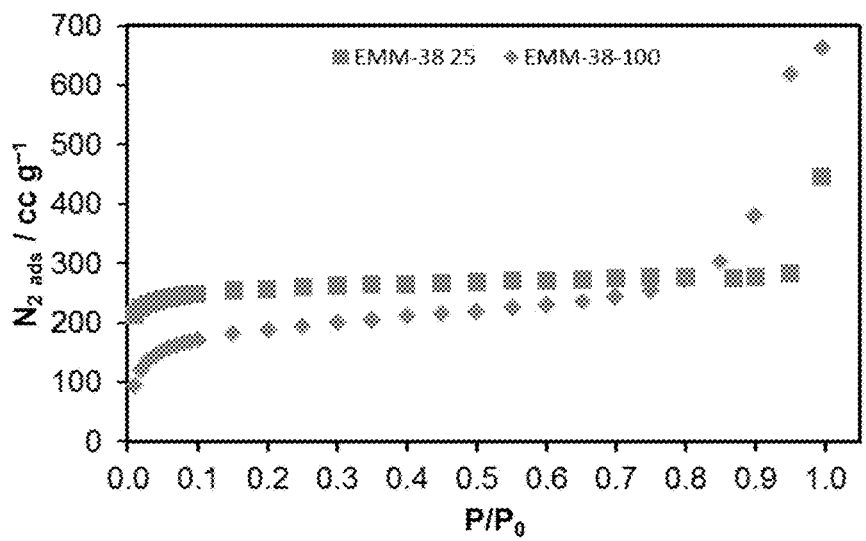
FIG. 11 shows $N_2$ adsorption isotherms conducted at 77 K on various EMM-38-## materials produced according to Example 3.

$N_2$ adsorption isotherms were conducted at 77 K on the EMM-38-## products and the results are shown in FIG. 11. In contrast to ZIF-11, EMM-38-## exhibits nitrogen-accessible pore volume at low temperatures.

Figure 12:
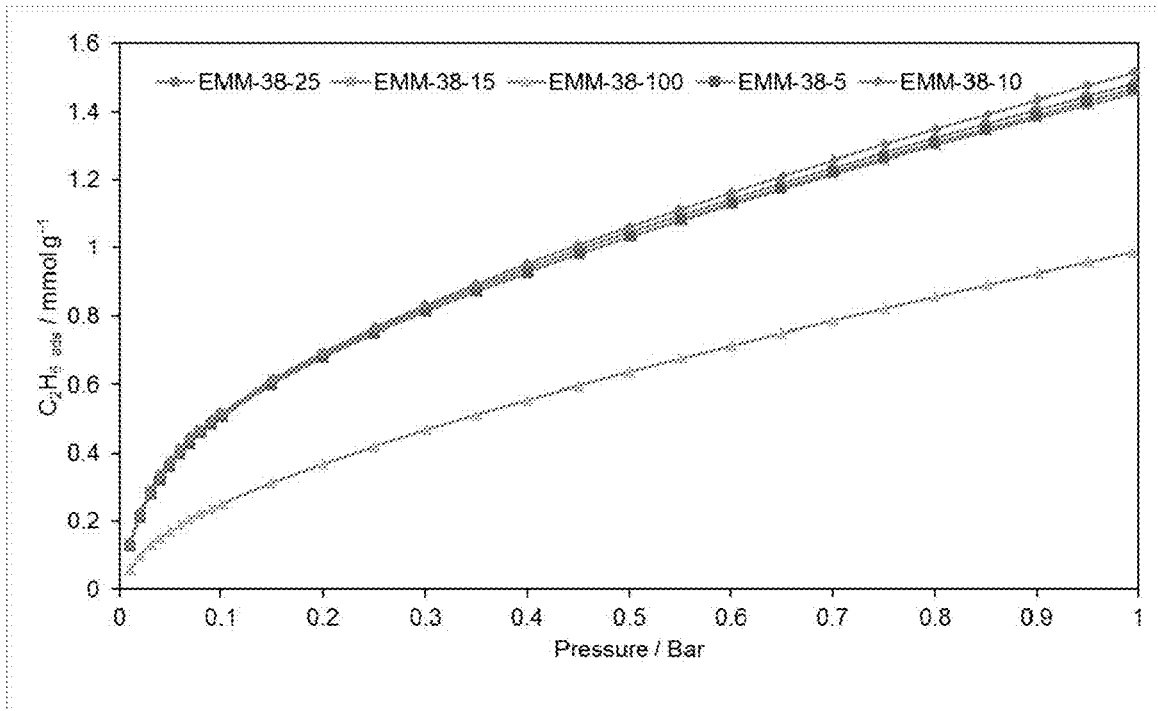
FIG. 12 shows ethane adsorption isotherms conducted at 30° C. on various EMM-38-## materials produced according to Example 3.

Ethane adsorption isotherms were conducted at 30° C. on the EMM-38-## products and the results are shown in FIG. 12. At modest contents of 4H-BIM, EMM-38-## exhibits isotherms very similar to that of ZIF-11. At higher 4H-BIM contents, the capacity for ethane decreases.

Example 4: Synthesis of EMM-38-100-N (N Signifies Presence of Nitrogen in the Partially Saturated Ring)

100 mg of 4,5,6,7-tetrahydro-3H-imidazo[4,5-c]pyridine and 100 mg of zinc acetate dehydrate were loaded into a 20 mL vial. To this, 0.1 mL of $NH_4OH$ (conc.) and 10 mL of ethanol was added. The reaction was stirred overnight at 60° C. The solids were then isolated via centrifugation and dried at 90° C.

Figure 13:
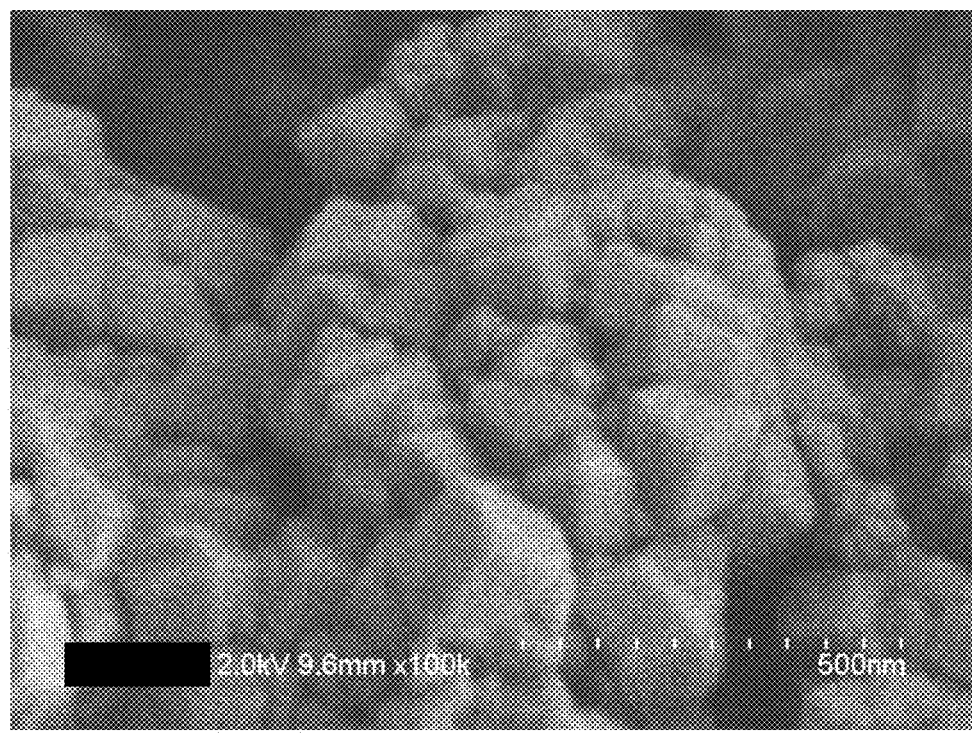
FIG. 13 shows a scanning electron micrograph (SEM) of the EMM-38-100-N material of Example 4.
Figure 14:
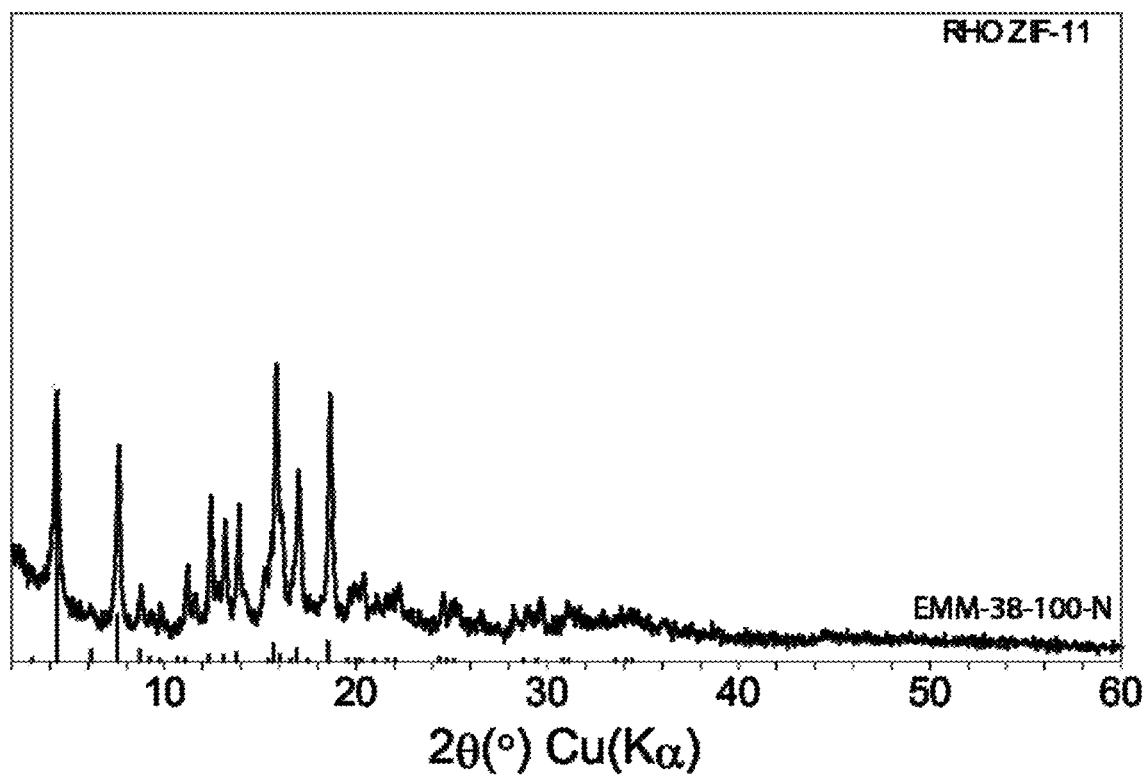
FIG. 14 shows a powder X-ray diffraction pattern of the EMM-38-100-N material of Example 4.

The SEM of the resultant EMM-38-100-N product is shown in FIG. 13. A powder X-ray diffraction pattern of the EMM-38-100-N product is shown in FIG. 14 and demonstrates the material has the RHO framework structure, closely isostructural with EMM-38-##.

Figure 15:
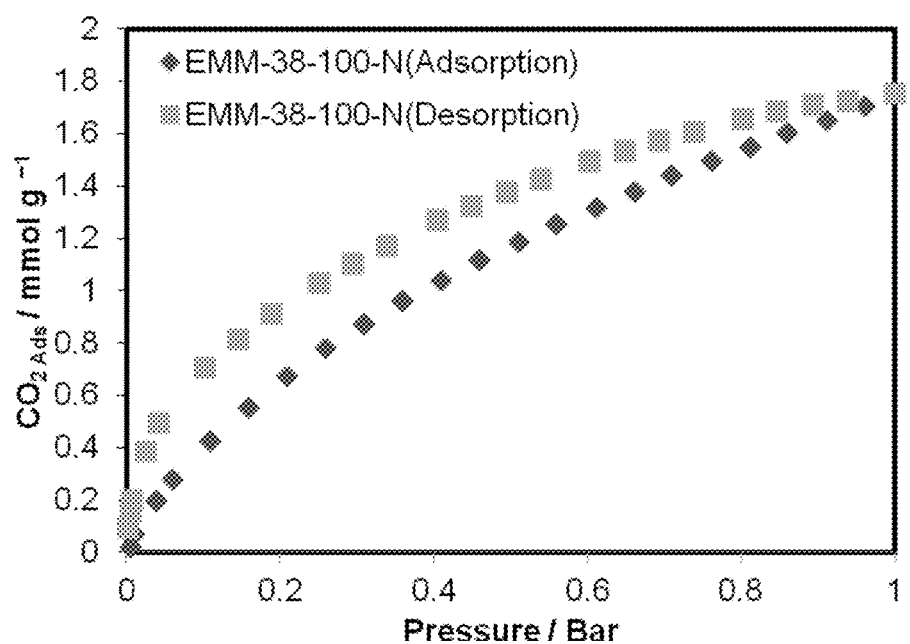
FIG. 15 shows $CO_2$ adsorption and desorption isotherms conducted at 30° C. on the EMM-38-100-N material of Example 4.

$CO_2$ adsorption and desorption isotherms were conducted at 30° C. on the EMM-38-100-N product and the results are shown in FIG. 15. What was notable is the higher capacity observed for EMM-38-100-N when compared to ZIF-11 or EMM-38-##.

The invention claimed is:

1. A zeolitic imidazolate framework material comprising zinc and 4,5,6,7-tetrahydrobenzimidazole.

2. The framework material of claim 1, further comprising benzimidazole or 5-azabenzimidazole.

3. The framework material of claim 2, further comprising from 0 mol % to 99 mol % of benzimidazole or 5-azabenzimidazole, based on the total amount of benzimidazole or 5-azabenzimidazole and 4,5,6,7-tetrahydrobenzimidazole or 4,5,6,7-tetrahydro-3H-imidazo[4,5-c]pyridine in the material.

4. The framework material of claim 1, further comprising an unsaturated benzimidazole or an unsaturated substituted benzimidazole as a linking ligand.

5. The framework material of claim 1, further comprising one or more divalent transition metal ions.

6. The framework material of claim 1, further comprising one or more zinc ions or one or more cobalt ions.

7. The framework material of claim 1, further comprising a 1:1 mixture of lithium and boron ions.

8. The framework material of claim 1, wherein said framework material exhibits the SOD framework type.

9. The framework material of claim 1, wherein said framework material exhibits the RHO framework type.

10. A zeolitic imidazolate framework material comprising zinc and 4,5,6,7-tetrahydro-3H-imidazo[4,5-c]pyridine.

11. The framework material of claim 10, further comprising benzimidazole or 5-azabenzimidazole.

12. The framework material of claim 11, further comprising from 0 mol % to 99 mol % of benzimidazole or 5-azabenzimidazole, based on the total amount of benzimidazole or 5-azabenzimidazole and 4,5,6,7-tetrahydrobenzimidazole or 4,5,6,7-tetrahydro-3H-imidazo[4,5-c]pyridine in the material.

13. A method of making a zeolitic imidazolate framework material comprising the step of reacting a mixture of a source of a partially saturated benzimidazole or a source of a partially saturated substituted benzimidazole with a source of zinc in the presence of a solvent at a temperature sufficient to form the zeolitic imidazolate framework material.

14. The method of claim 13 in which the temperature is at least 20° C.

15. The method of claim 13 in which the partially saturated benzimidazole comprises 4,5,6,7-tetrahydrobenzimidazole.

16. The method of claim 13 in which the partially saturated substituted benzimidazole comprises 4,5,6,7-tetrahydro-3H-imidazo[4,5-c]pyridine.

17. The method of claim 13, wherein the source of zinc comprises zinc acetate.

18. The method of claim 13, wherein the mixture further comprises an unsaturated benzimidazole or an unsaturated substituted benzimidazole.

* * * * *